United States Patent
Kipshidze et al.

(10) Patent No.: US 11,273,287 B2
(45) Date of Patent: Mar. 15, 2022

(54) SELECTIVELY DELIVERING PARTICLES INTO THE DISTAL PORTION OF THE LEFT GASTRIC ARTERY

(71) Applicant: Endobar Solutions, LLC, Orangeburg, NY (US)

(72) Inventors: Nickolas Kipshidze, New York, NY (US); Ronald Jay Solar, San Diego, CA (US)

(73) Assignee: Endobar Solutions LLC, Orangeburg, NY (US)

(*) Notice: Subject to any disclaimer, the term of this patent is extended or adjusted under 35 U.S.C. 154(b) by 315 days.

(21) Appl. No.: 14/597,398

(22) Filed: Jan. 15, 2015

(65) Prior Publication Data
US 2015/0133780 A1    May 14, 2015

Related U.S. Application Data

(63) Continuation-in-part of application No. 14/091,787, filed on Nov. 27, 2013.
(Continued)

(51) Int. Cl.
*A61M 25/00* (2006.01)
*A61M 25/10* (2013.01)
(Continued)

(52) U.S. Cl.
CPC ...... *A61M 25/007* (2013.01); *A61M 25/0029* (2013.01); *A61M 25/10* (2013.01);
(Continued)

(58) Field of Classification Search
CPC .............. A61M 25/10; A61M 25/007; A61M 2025/0183; A61M 2025/105; A61M 2025/1052; A61M 2025/1095
See application file for complete search history.

(56) References Cited

U.S. PATENT DOCUMENTS

| | | | | |
|---|---|---|---|---|
| 5,500,013 A | * | 3/1996 | Buscemi | A61F 2/82 604/104 |
| 5,669,880 A | * | 9/1997 | Solar | A61F 2/958 128/898 |

(Continued)

FOREIGN PATENT DOCUMENTS

| | | |
|---|---|---|
| DE | 19711935 | 4/1998 |
| JP | 2013512735 A | 4/2013 |
| WO | 0135858 | 5/2001 |

OTHER PUBLICATIONS

Casteel, B., Embolization procedure lowers levels of 'hunger hormone,' leads to weight loss, American College of Cardiology, Mar. 8, 2013.
(Continued)

*Primary Examiner* — Alexander J Orkin
(74) *Attorney, Agent, or Firm* — Potomac Law Group, PLLC

(57) ABSTRACT

Embolization particles can be safely delivered to the left gastric artery of a patient by introducing the distal end of a catheter in the patient's left gastric artery, inflating a balloon located near the distal end of the catheter so that the balloon prevents blood from flowing through the left gastric artery, and injecting a mixture of particles and contrast agent into the proximal end of the catheter so that they flow through the catheter. In addition, a path is provided for blood to flow into the catheter through an opening in the sidewall of the catheter at a position that is proximal to the balloon, and out through the distal end of the catheter. This blood flow helps to carry the particles along to their destination in the distal portion of the left gastric artery. The particles are also prevented from flowing into portions of the patient's artery system that are proximal of the balloon.

4 Claims, 6 Drawing Sheets

Related U.S. Application Data

(60) Provisional application No. 61/928,550, filed on Jan. 17, 2014, provisional application No. 61/775,070, filed on Mar. 8, 2013.

(51) Int. Cl.
*A61M 31/00* (2006.01)
*A61M 25/01* (2006.01)

(52) U.S. Cl.
CPC ... *A61M 31/005* (2013.01); *A61M 2025/0183* (2013.01); *A61M 2025/105* (2013.01); *A61M 2025/1052* (2013.01); *A61M 2025/1095* (2013.01); *A61M 2202/064* (2013.01); *A61M 2205/7545* (2013.01); *A61M 2210/12* (2013.01)

(56) References Cited

U.S. PATENT DOCUMENTS

| | | | | |
|---|---|---|---|---|
| 5,674,198 | A * | 10/1997 | Leone | A61M 25/1011 604/101.05 |
| 5,830,181 | A * | 11/1998 | Thornton | A61M 25/104 604/102.01 |
| 5,925,016 | A * | 7/1999 | Chornenky | A61M 25/09 604/19 |
| 6,139,517 | A * | 10/2000 | Macoviak | A61M 25/1002 604/101.05 |
| 6,193,685 | B1 | 2/2001 | Goodin | |
| 6,508,787 | B2 | 1/2003 | Erbel et al. | |
| 7,008,411 | B1 * | 3/2006 | Mandrusov | A61M 25/0084 604/164.01 |
| 7,402,320 | B2 | 7/2008 | Mirizzi et al. | |
| 2001/0031982 | A1 * | 10/2001 | Peterson | A61F 2/013 606/200 |
| 2002/0107479 | A1 | 8/2002 | Bates et al. | |
| 2002/0173819 | A1 | 11/2002 | Leeflang et al. | |
| 2003/0181864 | A1 * | 9/2003 | Deniega | A61M 25/0074 604/245 |
| 2004/0243057 | A1 * | 12/2004 | Vinten-Johansen | A61M 25/007 604/97.01 |
| 2008/0262467 | A1 * | 10/2008 | Humphrey | A61M 25/1011 604/500 |
| 2009/0187098 | A1 * | 7/2009 | Makower | A61B 1/0661 600/424 |
| 2009/0187144 | A1 | 7/2009 | Jayaraman | |
| 2009/0247868 | A1 * | 10/2009 | Chesnin | A61M 25/0032 600/435 |
| 2011/0130657 | A1 | 6/2011 | Chomas et al. | |
| 2011/0224628 | A1 * | 9/2011 | Bodenlenz | A61M 25/0012 604/264 |
| 2011/0282195 | A1 * | 11/2011 | Solar | A61M 25/0026 600/431 |
| 2011/0313340 | A1 * | 12/2011 | Judy | A61M 27/006 604/8 |
| 2012/0078188 | A1 * | 3/2012 | Hetke | A61M 25/007 604/173 |
| 2013/0096580 | A1 | 4/2013 | Cohn et al. | |

OTHER PUBLICATIONS

Arepally et al., Catheter-directed Gastric Artery Chemical Embolization for Modulation of Systemic Ghrelin Levels in a Porcine Model, Radiology, Jul. 2007, vol. 244 No. 1, pp. 138-143.
Arepally et al., Catheter-directed Gastric Artery Chemical Embolization Suppresses Systemic Ghrelin Levels in a Porcine Model, Radiology, Oct. 2008, vol. 249 No. 1, pp. 127-133.
Bawudun D. et al., Grelin Suppression and fat loss after left gastric artery embolization in canine model, Cardiovasc Intervent Radiol, Feb. 2012—7 pages, Full Version.
Cortez, Sealing the Artery with Hunger Hormone Cuts Pounds, Bloomberg, Mar. 7, 2013.
Bowdler, Electronic implant designed to reduce obesity to undergo trials, BBC News, Mar. 28, 2013.
Cummings, D, Ghrelin and Gastric Bypass: Is There a Hormonal Contribution to Surgical Weight Loss?, Journal of Clinical Endocrinology & Metabolism vol. 88, pp. 2999-3002 (2003).
Excelsior 1018 Microcatheter, Boston Scientific.
Guimaraes, et al., Does Material Matter? Particulate Embolics, Endovascular Today, Apr. 2013, pp. 70-74.
Harsch et al., Leptin and ghrelin levels in patients with obstructive sleep apnoea; effect of CPAP treatment, European Respiratory Journals, 2003.
Reinberg, Procedure Lowers 'Hunger Hormone' to Help Obese Lose Weight. US News and World Report, Mar. 8, 2013.
ACC: Gastric Artery Embolization Viable in Humans, Physician's Briefing, Health News Articles, 2013.
Terumo Heatrail II—Guiding Catheter.
Kipshidze, N., Endovascular Treatment of Obesity: Results from First in Man Study, Innovations in Cardiovascular Interventions Meeting, Dec. 2-4, 2012.
Kipshidze, N., Endevascular Treatment of Obesity: Early Results from First in Man Study, JACC: Cardiovascular Interventions, vol. 6, No. 2, Suppl. S, Feb. 23-26, 2013.
Kipshidze, N., First-in-Man Study of Left Gastric Artery Embolization for Weight Loss, JACC: Abstracts of Original Contributions, vol. 61, No. 10, Suppl. A, Mar. 12, 2013.
Morris, D, Embolization of the left gastric artery in the absence of angiographic extravasation, Cardio Vascular and Interventional Radiology, 1986, vol. 9, Issue 4, pp. 195-198.
Gastric artery embolization suppresses 'hunger hormone,' leads to weight loss, Yahoo Lifestyle India, Mar. 8, 2013.
International Search Report and Written Opinion in corresponding application PCT/US2015/011600 dated May 7, 2015, 13 pages.

* cited by examiner

SELECTIVELY DELIVERING PARTICLES INTO THE DISTAL PORTION OF THE LEFT GASTRIC ARTERY

CROSS REFERENCE TO RELATED APPLICATIONS

This application claims the benefit of U.S. Provisional Application 61/928,550 (filed Jan. 17, 2014); and this application is also a continuation-in-part of U.S. application Ser. No. 14/091,787 (filed Nov. 27, 2013), which claims the benefit of U.S. Provisional Application 61/775,070 (filed Mar. 8, 2013). Each of the above-identified applications is incorporated herein by reference in its entirety.

BACKGROUND

Obesity is widely recognized as a major public health issue resulting in decrease of quality of life and development of chronic diseases, such as metabolic syndrome, diabetes, hypertension, congestive heart failure, atherosclerosis, sleep apnea, etc. Lifestyle changes can be used to treat obesity, but lifestyle changes are not always achievable, especially in long term prospect. Drug therapy is one conventional treatment for obesity, but it is often accompanied by various complications and adverse side effects.

Bariatric surgery is another conventional treatment for obesity. One of the recognized benefits of bariatric surgery is the decreased production of ghrelin. Ghrelin, a neuropeptide which is predominantly produced in the gastric fundus, is the only known hormone that stimulates food intake (orexigenic hormone). It is believed that the decreased production of ghrelin that is associated with bariatric surgery helps promote weight loss. But bariatric surgery is invasive and can be accompanied by considerable surgical complications and/or adverse side effects.

SUMMARY OF THE INVENTION

One aspect of the invention is directed to a method of delivering embolization particles to the left gastric artery of a patient via a catheter that has a distal end, a proximal end, a sidewall, and a first lumen that provides a path between the proximal end and the distal end. This method includes the steps of: introducing the catheter into the patient so that the distal end of the catheter is positioned in the patient's left gastric artery; inflating a balloon located near the distal end of the catheter so that the balloon prevents blood from flowing through the left gastric artery; injecting a mixture of particles and contrast agent into the proximal end of the catheter so that the particles and contrast agent flow through the catheter and out though the distal end of the catheter; providing a path for blood to flow into the catheter through an opening in the sidewall of the catheter at a position that is proximal to the balloon, and out through the distal end of the catheter; and preventing the particles from flowing into portions of the patient's artery system that are proximal of the balloon. The blood flow helps to carry the particles along to their destination in the distal portion of the left gastric artery.

In some embodiments of this method, the first lumen provides a fluid-tight path between the proximal end and the distal end of the catheter, and the step of providing a path for blood to flow is implemented by a second lumen that is distinct from the first lumen. In some embodiments of this method, the preventing step is implemented using a strainer disposed at the proximal end of the second lumen. Preferably, the strainer comprises a mesh having a mesh spacing between 150 and 250 microns. In other embodiments of this method, the preventing step is implemented using a strainer disposed at the distal end of the second lumen. Preferably, the strainer comprises a mesh having a mesh spacing between 150 and 250 microns.

The step of providing a path for blood to flow may be implemented using an opening in the sidewall of the catheter at a position that is proximal to the balloon that permits blood to flow into the first lumen, and the preventing step may be implemented using a strainer disposed at the opening. Preferably, the strainer comprises a mesh having a mesh spacing between 150 and 250 microns.

In some embodiments of this method, the opening in the sidewall is disposed at a position such that when the distal end of the catheter is positioned in the patient's left gastric artery, the opening in the sidewall will be positioned in the patient's left gastric artery. In other embodiments of this method, the opening in the sidewall is disposed at a position such that when the distal end of the catheter is positioned in the patient's left gastric artery, the opening in the sidewall will be positioned in the patient's celiac artery.

Another aspect of the invention is directed to a catheter for delivering embolization particles to a target artery of a patient. This catheter has a distal end and a proximal end, and the catheter includes (1) a first lumen that provides a fluid-tight path for particles to flow between the proximal end of the catheter and the distal end of the catheter; (2) a balloon located near the distal end of the catheter, with the balloon configured so that when the balloon is inflated, the balloon prevents blood from flowing through the target artery; (3) an inflation lumen that is used to inflate the balloon, the inflation lumen having a distal end that is in fluid communication with an interior of the balloon; (4) a second lumen that has an input port that is located proximal to the balloon and an output port that is located distal to the balloon, with the second lumen configured to provide a fluid-tight path for blood to flow from the input port to the output port; and (5) a strainer that prevents the particles from flowing through the second lumen. The input port is disposed at a position such that when the distal end of the catheter is positioned in the target artery, blood from an artery in the patient's body can enter the second lumen via the input port, flow through the second lumen, exit the second lumen via the output port, and flow from the output port into the target artery. This blood flow helps to carry the particles along to their destination in the target artery.

In some embodiments, the strainer is disposed at the input port of the second lumen. In other embodiments, the strainer is disposed at the output port of the second lumen. Preferably, the strainer is coarse enough to permit all types of blood components to pass. Preferably, the strainer comprises a mesh having a mesh spacing between 150 and 250 microns.

In some embodiments, the target artery is a left gastric artery, and the distal end of the catheter and the balloon are configured for insertion into the left gastric artery.

Another aspect of the invention is directed to a catheter for delivering embolization particles to a target artery of a patient. This catheter has a distal end, a proximal end, and a sidewall, and the catheter includes (1) a first lumen that provides a path for particles to flow between the proximal end of the catheter and the distal end of the catheter; (2) a balloon located near the distal end of the catheter, with the balloon configured so that when the balloon is inflated, the balloon prevents blood from flowing through the target artery; (3) an inflation lumen that is used to inflate the balloon, the inflation lumen having a distal end that is in fluid communication with an interior of the balloon; (4) an opening into the first lumen through the sidewall of the catheter, the opening located proximal to the balloon, and (5) a strainer disposed at the opening, the strainer configured to prevent the particles from exiting the first lumen via the opening. The opening is disposed at a position such that when the distal end of the catheter is positioned in the target artery, blood from an artery in the patient's body can flow into the opening, through the first lumen, and into the target artery. This blood flow helps to carry the particles along to their destination in the target artery.

Preferably, the strainer is coarse enough to permit all types of blood components to pass. Preferably, the strainer comprises a mesh having a mesh spacing between 150 and 250 microns.

In some embodiments, the target artery is a left gastric artery, and the distal end of the catheter and the balloon are configured for insertion into the left gastric artery.

DETAILED DESCRIPTION OF THE PREFERRED EMBODIMENTS

Figure 1:
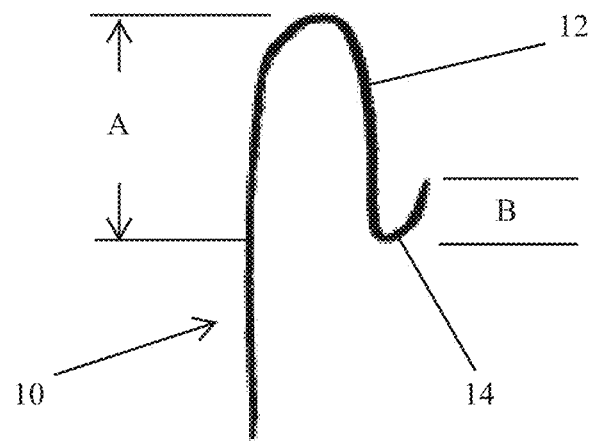
FIG. 1 depicts an example of a suitable shape for the distal end of a custom-shaped guiding catheter with an S-shaped bend.

Percutaneous endovascular modification of the function of the gastric fundus using particulate embolization of the distal portion of the left gastric artery is less invasive and more cost effective alternative to bariatric surgery for achieving weight loss.

U.S. application Ser. No. 14/091,787 describes a novel approach which involves modifying the arterial blood flow to the gastric fundus by means of percutaneous endovascular flow reduction (or interruption) in the distal portion of the left gastric artery. Experiments in humans (performed outside the U.S.) has demonstrated dramatic weight loss at one month after procedure and sustained for six months follow-up with no reported adverse effects. While reduction in the hunger-mediating peptide hormone ghrelin (secreted in the gastric fundus) has been identified as a one of possible mechanism, the complete physiologic mechanism is not yet clear and may well involve other hormones and/or changes in gastric motility with consequent reduction in hunger sensation in experimental subjects.

The approach described herein achieves endovascular flow reduction or interruption by introducing a plurality of particles into the distal portion of the subject's left gastric artery. The particles, also referred to herein as microparticles, preferably have sizes between 300 and 500 µm, and are delivered via a microcatheter. The particles are preferably compressible and spherical. They are preferably made of polyvinyl alcohol, and more preferably made of acrylamido polyvinyl alcohol. One suitable commercially available product for this purpose is BeadBlock Embolic Beads, 300-500 µm compressible microspheres (Biocompatibles UK Limited, Surrey, UK).

Alternative commercially available products for this purpose include polyvinyl alcohol (PVA foam embolization particles, Cook Medical, Bloomington, Ind.); hydrogel core with Polyzene-F coating (Embozene™ microspheres, CeloNova Biosciences, Inc., San Antonio, Tex.); microspheres made from trisacryl cross linked with gelatin (Embosphere microspheres, Merit Medical Systems, Inc., South Jordan, Utah); HepaSphere™ Microspheres, which are made from two monomers (vinyl acetate and methyl acrylate) that combine to form a copolymer (sodium acrylate alcohol copolymer); Bearing™ nsPVA Embolization Particles, which are irregularly-shaped, biocompatible, hydrophilic, nonresorbable particles produced from polyvinyl alcohol; EmboGold™ Microspheres, which are made from trisacryl cross linked with gelatin and impregnated with 2% elemental gold for visibility; QuadraSphere™ Microspheres, which are also made from two monomers (vinyl acetate and methyl acrylate) that combine to form a copolymer (sodium acrylate alcohol copolymer), and Terumo Bead BlockT microspheres. In alternative embodiments, other embolization materials may be used, including but not limited to coils, other microparticles, foams, different synthetic or organic gels, thrombin, fibrin, collagen, fibrinogen (liquid or powder), and any other material that can occlude blood vessel.

Optionally, certain substances may be added to the particles (or to the other embolization materials) to enhance the effect of the procedure. Examples include, but are not limited to: pharmaceuticals, genetic materials, or different types of cells that also help to decrease production of ghrelin and/or other hormones or other substances that effect appetite in humans.

One procedure involves inserting a catheter into the left gastric artery, which is the major vessel that supplies gastric fundus and modify blood flow. One way to accomplish this is to insert a guiding catheter via the femoral artery or radial artery until the left gastric artery is engaged (in other words, until the distal end of the guiding catheter is introduced into the subject's left gastric artery.) Although the inventor is not aware of any guiding catheters that are specially designed to engage the left gastric artery, examples of suitable guiding catheters for this step include catheters that are already available for other applications such as for coronary angiography and or coronary stenting. In one preferred embodiment, the guiding catheter is a 6 French Heartrail II JR-4.0 guiding catheter (Terumo Europe N.V., Leuven, Belgium). That particular guiding catheter is a Judkins Right type catheter and has a JR-4.0 shape code. In alternative embodiments, a custom-shaped guiding catheter may be used for obtaining easy access to left gastric artery. An example of one suitable shape for such a guiding catheter is provided in FIG. 1, in which the distal end 12 of the custom-shaped guiding catheter 10 has an S-shaped bend. This shape is similar to the shape of the Surefire Axis Catheter (Surefire Medical Inc., Westminster Colo.), but the distal-most bend 14 is increased from about 45° to about 160°. Suitable dimensions for the guiding catheter 10 for accessing the left gastric artery are as follows: A between 3 and 4 inches; and B between ½ and 1 inch.

After the guiding catheter is in position, a guidewire is then guided through the guiding catheter and introduced into the mid segment or distal portion of the subject's left gastric artery, and then a microcatheter is advanced over the guidewire. Once the distal end of the microcatheter has been inserted into the mid segment or distal portion of left gastric artery, the embolization material is delivered into the distal portion of left gastric artery via the microcatheter. The distal shaft of the microcatheter must be small, e.g., 2 French in diameter. One example of a commercially available microcatheter that is suitable for this purpose is the Excelsior 1018 Microcatheter (Boston Scientific Corp., Corck, Ireland).

The presence of the embolization material in the distal portion of left gastric artery will reduce or interrupt the blood flow in the distal portion of left gastric artery, which will modify the blood supply to the fundus of stomach. More specifically, it will reduce or interrupt the blood supply to the fundus.

Using microparticles for the embolization material (as opposed to other types of embolization materials) is advantageous because they are inert, biocompatible, and flow-directed. Moreover, when used as described herein, they will not cause tissue necrosis or unwanted non-target embolization. In contrast, if a chemical-based embolization material such as sodium morrhuate is used instead of the preferred microparticles, deep penetration and or extravasation of this sclerotherapy agent into the gastric tissue may lead to local edema and/or extensive inflammation that results in gastric ulceration and necrosis. Chemical-based embolization material may also lead to systemic toxicity and non-target embolization that may damage the liver, spleen or other organs.

Using particles with sizes between 300 and 500 µm is advantageous because using smaller particles (e.g., 50-100 µm) can result in mucosal necrosis of the fundus, and gastric ulcers. It can also result in non-target embolization of, for example, the esophagus, the liver, and/or the spleen because the small particles can penetrate very deep into tissue and destroy gastric mucosa. Animal experiments have shown that such smaller particles may also end up in structures other than the fundus. In addition, using larger particles (e.g., 700-1000 µm) can result in gastric ulcers, and non-target embolization of, for example, the esophagus, the liver, and/or the spleen. This may be due to deformation of the particles during injections and the formation of larger clusters, which can lead to more proximal embolization. It may also be due to reflux of the particles due to the Venturi effect. In contrast, when particles with sizes between 300 and 500 µm are used, these problems are avoided or at least minimized.

Limiting the delivery of the particles to the distal portion of the subject's left gastric artery is advantageous because when the proximal portion of the left gastric artery is also filled with particles, the risk of esophageal and nonfundus gastric ulcers is very high. More specifically, it was observed in three out of three subjects in animal studies, when tested in pigs. In contrast, these problems were not observed in any of the three pig subjects in which the delivery of the particles was limited to the distal portion of the test subject's left gastric artery.

Thus, by using the correct size of the correct material and delivering it to the correct location, many of the problems associated with other approaches are avoided, and the procedure can be made safe.

Example 1

A study was done on five obese subjects to determine the feasibility, safety, and efficacy of embolization of the distal portion of the left gastric artery to reduce plasma ghrelin levels and body weight.

All subjects underwent gastroscopy prior the embolization to assess for the presence of peptic ulcer or gastritis. Gastritis was found in two subjects who subsequently underwent medical treatment. Embolization was performed only after follow-up gastroscopy showed significant improvement in mucosal irritation.

Weights were measured and routine blood samples obtained including a complete blood count, electrolytes, and creatinine prior to embolization.

In the procedure, 6-Fr femoral access was obtained. More specifically, a 6-Fr Heartrail II JR-4.0 guiding catheter (Terumo Europe N.V., Leuven, Belgium) was used to engage the celiac trunk ostium and angiography performed in different projections in order to identify the origin and anatomy of left gastric artery. In some cases, a 0.35" guidewire was advanced into the common hepatic or splenic arteries to stabilize the guiding catheter position.

Figure 5:
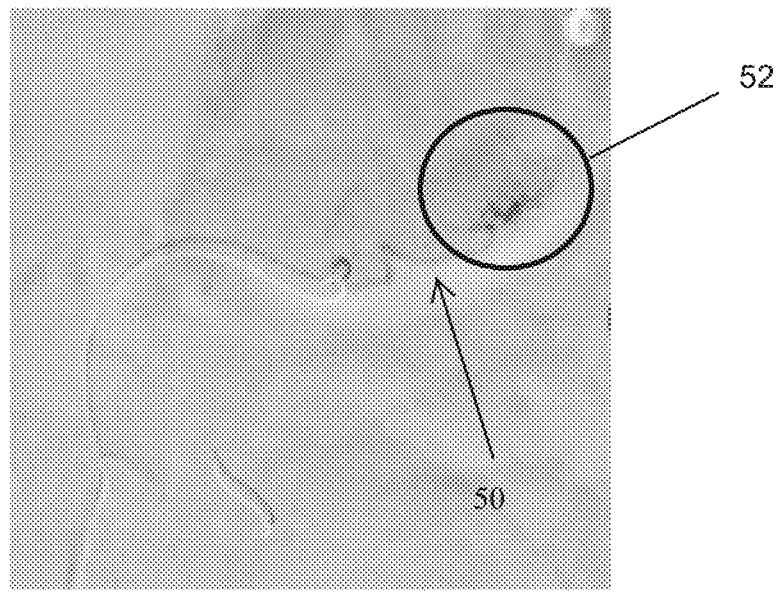
FIG. 5 depicts an angiography of a left gastric artery before the microparticles were delivered to their destination.

The left gastric artery, a branch of the celiac trunk, was wired with a 0.014" Runthrough NS PTCA Guide Wire (Terumo Europe N.V., Leuven, Belgium) and an Excelsior 1018 Microcatheter (Boston Scientific Corp., Corck, Ireland) advanced over the guide wire into the mid segment of the left gastric artery. Subsequently, the guide wire was removed while maintaining the microcatheter position in the left gastric artery and selective angiography performed to ensure proper catheter position and define the anatomy and course of the left gastric artery. FIG. 5 is an angiography of the left gastric artery 50 and the surrounding anatomy after a radio-opaque material was injected into the left gastric artery, but prior to the injection of any particles. The dark artifacts in the circle 52 reveal that blood is flowing in the distal portion of the left gastric artery.

Figure 6:
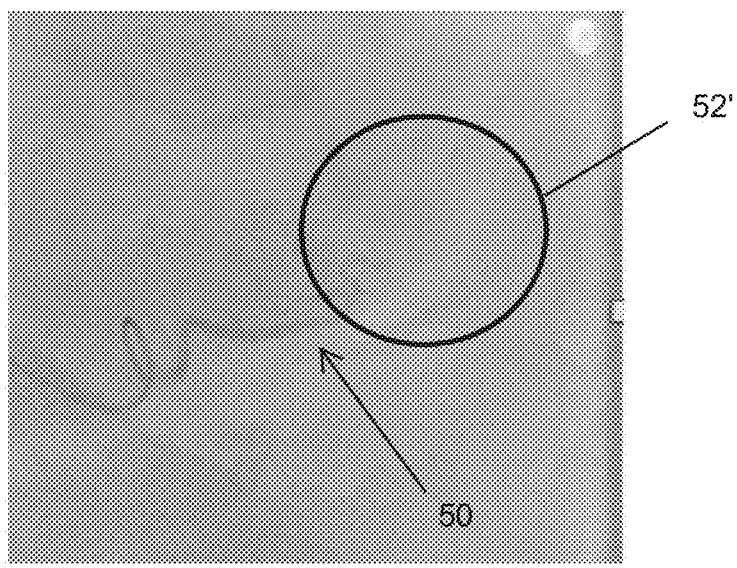
FIG. 6 depicts an angiography of the left gastric artery after the distal portion of that artery was filled with microparticles.

Repeat injections of small amounts of BeadBlock Embolic Bead, 300-500 µm compressible microspheres (Biocompatibles UK Limited, Surrey, UK) mixed with contrast agent (1:1 ratio) were then performed. Angiography was performed between injections of the microspheres to assess left gastric artery flow characteristics. The injection of the microspheres was continued until distal portions of artery branches were no longer visible during radio-opaque contrast injection. This is shown in FIG. 6, which depicts the left gastric artery 50 and the surrounding anatomy. Note the absence of dark artifacts in the circle 52', which indicates that blood is no longer flowing in the distal portion of the left gastric artery.

The guiding and microcatheter were then withdrawn and subjects transferred to a ward, where the introducer sheath was removed and manual pressure applied to obtain hemostasis.

Esophagogastroscopy was performed in all subjects before and after the procedure gastroscopy. A second follow-up gastroscopy was performed one week after the procedure. Weight and fasting plasma ghrelin levels were obtained at baseline and the 1, 3, and 6-month follow-up visits. To obtain the ghrelin levels, clotted blood samples were centrifuged to separate out blood plasma. Fasting levels of ghrelin, ALT, AST, urea and uric acid were then measured. Ghrelin was measured using the Human Ghrelin (TOTAL) RIA KIT (Merck Millipore). Subject's weight and body mass index (BMI) was also calculated at each of the visits.

Figure 2:
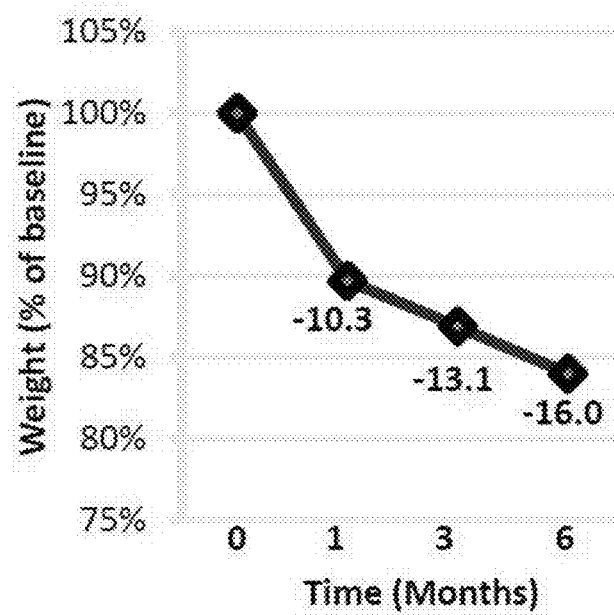
FIG. 2 is a graph that shows how the weight of the subjects changed over time.
Figure 3:
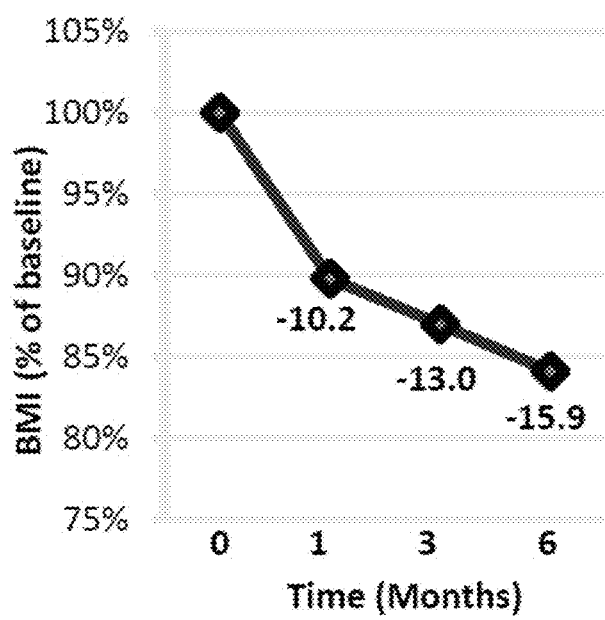
FIG. 3 is a graph that shows how the BMI (body mass index) of the subjects changed over time.
Figure 4:
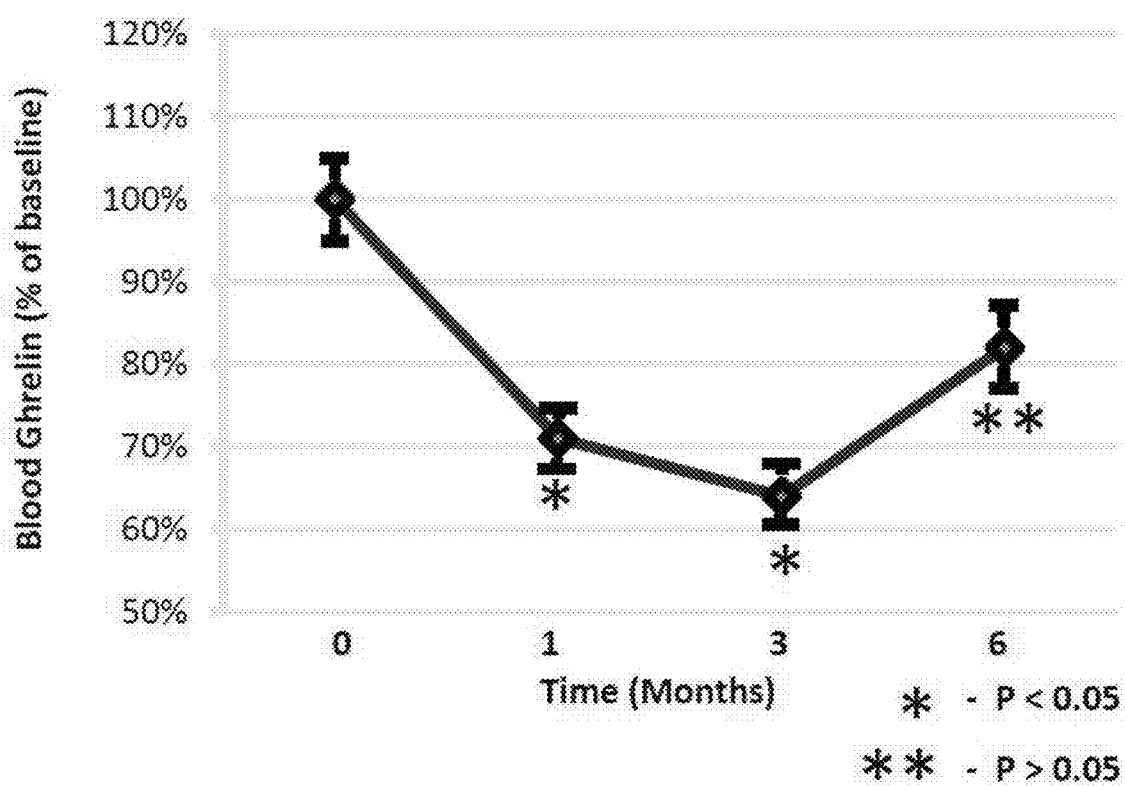
FIG. 4 is a graph that shows how the ghrelin level in the subjects' blood changed over time.

Data for the study is presented below. Table 1 shows the subject data, Table 2 shows the weight at each visit for each subject, Table 3 shows the corresponding BMI, and Table 4 shows the ghrelin levels at each visit for each subject. FIGS. 2, 3, and 4 depict the data in Tables 2, 3, and 4, respectively, in a graphical format.

TABLE 1

| Parameter | Value |
| --- | --- |
| Number of participants | 5 |
| Gender female/male (%) | 20/80% |
| Age female/male (years) | 44.7 ± 7.4 |
| Weight (kg) | 128.1 ± 24.4 |
| BMI (kg/m2) | 42.2 ± 6.8 |
| Ghrelin (pg/ml) | 473.4 ± 189.11 |

TABLE 2

| Subject # | Initial weight (kg) | Weight at 1 month FU | Weight at 3 month FU | Weight at 6 month FU |
| --- | --- | --- | --- | --- |
| 1 | 119 | 102 | 99 | 94 |
| 2 | 165 | 146 | 143 | 140 |
| 3 | 98 | 90 | 85 | 80 |
| 4 | 131 | 120 | 116 | 117 |
| 5 | 127 | 117 | 114 | 107 |
| Mean | 128 ± 24 | 115 ± 21 | 111 ± 22 | 108 ± 23 |
| p Value | | 0.0032 | 0.0012 | 0.0008 |

TABLE 3

| Subject # | Initial BMI | BMI at 1 month FU | BMI at 3 month FU | BMI at 6 month FU |
| --- | --- | --- | --- | --- |
| 1 | 42 | 36 | 35 | |
| 2 | 53 | 47 | 46 | 45 |
| 3 | 34 | 31 | 30 | 28 |
| 4 | 41 | 38 | 37 | 37 |
| 5 | 41 | 38 | 38 | 34 |
| Mean | 42 ± 7 | 38 ± 6 | 37 ± 6 | 36 ± 6 |
| p Value | | 0.0033 | 0.0012 | 0.001 |

TABLE 4

| Subject # | Initial Ghrelin level (pg/ml) | Ghrelin level at 1 month FU | Ghrelin level at 3 month FU | Ghrelin level at 6 month FU |
| --- | --- | --- | --- | --- |
| 1 | 459.6 | 313.4 | 301.3 | 325.5 |
| 2 | 486.1 | 325.9 | 323.6 | 410.9 |
| 3 | 445.5 | 380.7 | 315.8 | 389.1 |
| 4 | 501.2 | 341.6 | 299.7 | 388.6 |
| 5 | 478.3 | 342.2 | 325.5 | 391.3 |
| Mean | 470.54 | 340.76 | 314.18 | 381.08 |
| p Value | | 0.0015 | 0.0002 | 0.0042 |

STATISTICAL ANALYSIS: Statistical analysis was performed using computer software (SPSS 12.0 for Windows, Lead Technologies Inc. 2003. Chicago, Ill.). All values were presented as the mean±standard deviation (±SD). Comparison of weights and plasma ghrelin levels between different time points were done with the paired t-test. A p-value of <0.05 was considered to determine statistical significance RESULTS: There were no procedural complications. Three of the five subjects described mild transient epigastric pain after the procedure. However, follow-up gastroscopies on the day after embolization and at 1-week follow-up did not reveal any abnormalities. All subjects reported a significantly decreased appetite in the first days after the procedure.

Significant progressive weight loss accompanied by reductions in plasma ghrelin levels was observed in all subjects at all follow-ups: Mean weight and BMI was reduced by 10%, 13%, and 16% at 1-, 3- and 6-month follow-up, respectively (Table 2 and 3). Mean initial weight (128.12±24.4 kg) decreased to 108±23 kg (p<0.001). Blood plasma ghrelin levels (initially 473±189) were significantly lower at 1- and 6-month follow-up (by 29% and 36% from baseline, p<0.05) and increased slightly at the 6-month follow-up compared with 3-month follow-up while remaining 18% lower from the baseline (p>0.05).

Figure 7:
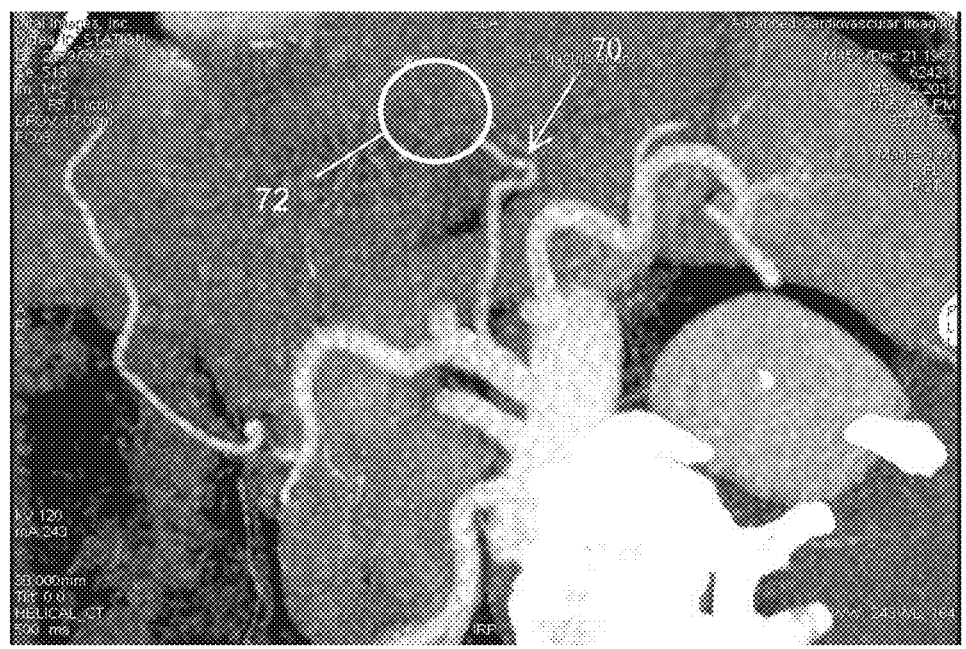
FIG. 7 depicts a CT angiography of the left gastric artery and the surrounding region three months after the distal portion of that left gastric artery was filled with microparticles.

FIG. 7 is a CT angiograph the left gastric artery 70 and the surrounding anatomy that was taken 3 months after procedure. In this figure, portions where blood is flowing are indicated in white. Because the distal portion of the left gastric artery is not visible in region 72, it is apparent that the distal portion remains occluded 3 months after procedure.

The data above demonstrates that embolization of the distal portion of the left gastric artery using microparticles is associated with significant reductions in plasma ghrelin levels and weight loss in humans. It should be noted, however, that after an initial pronounced decline in ghrelin levels after the procedure, the levels did increase at the last follow-up visit (i.e., at the 6 month visit), Although the levels were still lower than the pre-procedure baseline, a long-term study may be warranted to further investigate this increase.

The procedure described above appears to be safe. Specifically, there were no incidences of ulcer formation or injury to remote structures. This may be related to the selective injection into the left gastric artery of beads that are large enough in size as to not allow systemic or remote toxicity, yet small enough to avoid the potential problems described above. Note that with more extensive embolization of arteries other than the left gastric artery, the ulcer risk may be higher. For example, 40% of animals that underwent embolization of the left, short, and accessory gastric arteries developed gastric ulcers in a study by Paxton et al. These ulcers were located at the lesser curvature, suggesting a watershed effect. In addition, using the correct embolic materials as described herein apparently minimizes the extent and likelihood of injury to adjacent or remote tissue.

It should be noted that this example was a non-randomized single-arm feasibility, safety, and efficacy trial with all its inherent limitations. First, the absence of a control group does not allow definitive conclusions regarding efficacy. It is possible that the procedure and study participation led to a higher motivation for diet control and exercise. However, in this case, a decrease in plasma ghrelin levels should not be expected. Second, the intermediate-term follow-up (i.e., 6 months) is too short to make conclusions regarding long-term weight loss, as a rebound phenomenon with recurrent weight gain is conceivable. Third, though not observed in a study by the inventor, a risk of gastric ulcer formation may be significant but too small to have been observed in the study.

It can therefore be concluded that Percutaneous embolization of the distal portion of the left gastric artery with embolic beads is feasible and appears to be safe. It leads to a reduction in plasma ghrelin levels and is accompanied by a significant weight loss at intermediate term follow-up. It may be a good tool to enhance weight loss in subjects with morbid obesity who cannot achieve weight loss by conventional means (diet and exercise) and an alternative to or complimentary to bariatric surgery.

Although the procedure described above in has many benefits, a potential problem exists: if too many particles are delivered through the catheter, reflux of the particles may occur. More specifically, even though the distal end of the catheter might be properly positioned in the mid segment or distal portion of left gastric artery, when too many particles are injected through the catheter, the particles can back up to more proximal portions of the left gastric artery. And if the number of particles is even larger, the particles could back up all the way to the celiac artery. This could be dangerous because the particles could then travel forward to the liver, spleen, or pancreas. It is therefore preferable to make special provisions to prevent reflux of the particles, so that the particles do not travel to other parts of the body.

Figure 8:
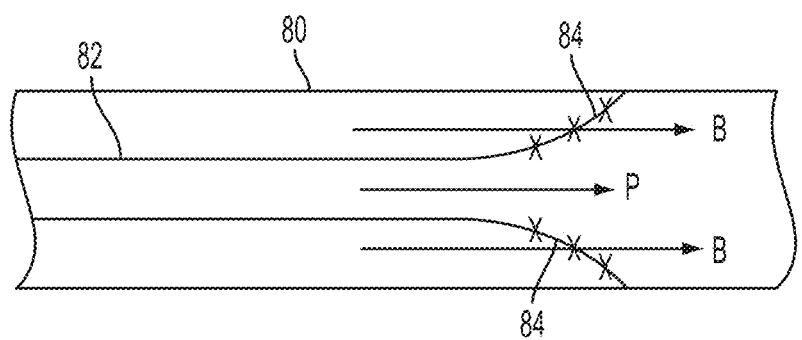
FIG. 8 depicts the distal end of a commercially available catheter that may be used to prevent reflux of the microparticles.

FIG. 8 depicts the distal end of a commercially available catheter (made by Surefire Medical Inc.) that can be used to prevent reflux. In this embodiment, the wall 82 of the catheter defines an internal lumen, and the particles are delivered through that lumen, as indicated by the arrow labeled P. The distal end 84 of the catheter flares out and preferably touches the inner walls of the artery 80 on all sides of the catheter. At least a portion of the flared distal end 84 is made of mesh, indicated by the "xxx" marking in FIG. 8. The mesh size is selected so that all types of blood component cells can pass (including red blood cells, white blood cells, etc.), but the microparticles cannot pass. The mesh at the flared distal end 84 therefore prevents the particles from traveling backwards. A suitable spacing for the mesh for this purpose is between 150 and 250 microns, and preferably about 200 microns. As a result, even though the flared distal end 84 of the catheter touches the walls of the artery 80, blood can still flow as indicated by the arrows B. The flow of blood is desired because the blood flow helps to carry the particles along to their destination in the distal portion of the left gastric artery. However, because the left gastric artery has a relatively small diameter, the body of the catheter will block a large portion of the artery, which will reduce the amount of blood that can flow past the catheter. In this embodiment, the blood flow could be reduced to the point where the blood flow will not adequate to direct the particles to their desired destination.

Figure 9A:
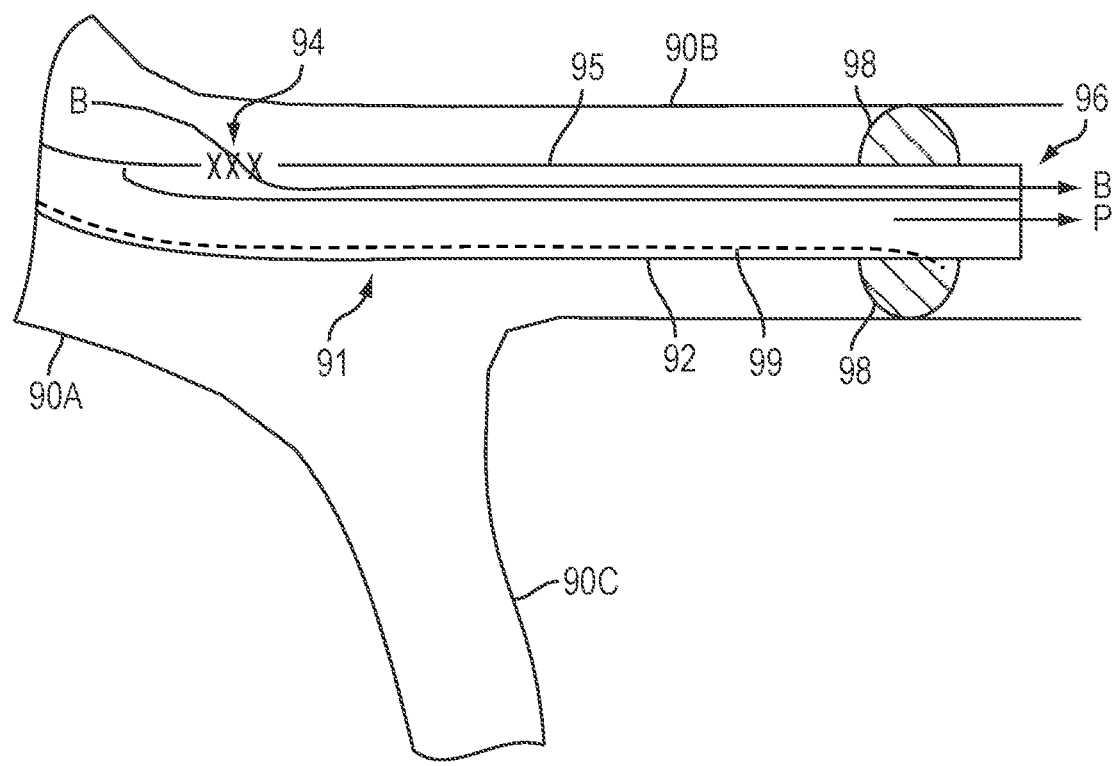
FIG. 9A depicts the distal end of an improved catheter that is designed to prevent reflux.

FIG. 9A depicts the distal end of a novel catheter that is designed to overcome this problem by maintaining significant blood flow that is sufficient to carry the particles to their desired destination, while still preventing reflux of the particles. In this embodiment, the wall 92 of the catheter 91 defines a first internal lumen, and the particles are delivered through that first internal lumen, as indicated by the arrow labeled P. This lumen provides a fluid-tight path for particles to flow between the proximal end of the catheter (not shown) and the distal end of the catheter. The outer diameter of the catheter 91 is preferably between 0.038 and 0.064 inches, and is more preferably about 0.05 inches. The diameter of the first internal lumen is preferably between 0.012 and 0.020 inches, and is more preferably about 0.016 inches. The first internal lumen is preferably tracked over a guidewire (not shown) to facilitate safe positioning of the catheter 91 to the desired location. Optionally, to facilitate catheter advancement in the blood vessel and to prevent kinking, the wall 92 of the catheter 91 may contain a longitudinally embedded core-wire (not shown) which may be tapered to impart varying degrees of longitudinal flexibility.

A balloon 98 located near the distal end of the catheter can be inflated in a conventional manner (e.g., via a dedicated inflation lumen 99 that has a distal end that is in fluid communication with an interior of the balloon), and the balloon will prevent any particles from refluxing. The balloon is preferably between 2 and 15 mm long in a proximal to distal direction, and is more preferably between 5 and 10 mm long. The balloon is preferably located between 2 and 20 mm from the distal end of the catheter 91, and is more preferably about 10 mm. The balloon 98 is preferably inflated with very low pressure (less than 1 atm), and is preferably designed to fail at low pressure (greater than 2 atm) in order to prevent barotrauma to the blood vessel. Optionally, the balloon and catheter preferably may have a hydrophilic-heparin coating to further minimize vascular trauma. The balloon 98 may be made from a compliant or semi-compliant material, such as polyurethane, polyimide, polyolefins, silicone, or copolymers thereof. The balloon 98 is preferably designed such that the diameter may be adjusted in a slow, continuous manner by varying the volume of inflation media in order to occlude varying vessel diameters.

When the balloon 98 is inflated, the natural flow of blood through the left gastric artery is blocked (i.e., the balloon prevents blood from flowing through the target artery), which would ordinarily not be desirable because the blood flow help carry the particles along to their destination. To remedy this issue, a second lumen 95 is provided in this embodiment. The second lumen 95 has an input port 94 that is proximal to balloon 98, and an output port 96 that is distal to the balloon 98. This second lumen provides a fluid-tight path for blood to flow from the input port to the output port. Blood will enter the second lumen 95 through the input port 94 and exit the second lumen 95 through output port 96, as indicated by the arrow labeled B-B. The diameter of second lumen is preferably between 0.006 and 0.014 inches, and is more preferably about 0.010 inches. Preferably, at least one of the ports 94, 96 is fitted with a strainer (indicated by the "xxx" marking in FIG. 9A) that prevents the particles from flowing through the second lumen. A preferred approach for implementing the strainer is to use a mesh with a mesh size that is coarse enough to permit all types of blood component cells to pass (including red blood cells, white blood cells, etc.), but fine enough to prevent the microparticles from passing. A suitable spacing for the mesh for this purpose is between 150 and 250 microns, and preferably about 200 microns. Alternatively, a finer mesh that only permits the red blood cells to pass may be used. Preferably, the mesh includes filaments in two perpendicular directions (i.e., arranged like the wires in a conventional window screen). In alternative embodiments, the strainer may be made of filaments that intersect at non-perpendicular angles. In other alternative embodiments, the strainer may be made of a plurality of filaments that are all parallel (i.e., arranged like the strings of a harp), the strainer may also be configured like a colander, or the strainer may be implemented using a semipermeable membrane with a suitable pore size.

Due to the second lumen 95, blood from an artery in the patient's body can enter the second lumen via the input port, flow through the second lumen, exit the second lumen via the output port, and flow from the output port into the left gastric artery. Thus, blood can flow forward through the artery 90B even though the balloon 98 is inflated. The flow of blood through the second lumen 95 will be sufficient to carry the particles along to their destination in the distal portion of the left gastric artery. In some preferred embodiments, the length of the second lumen 95 is long enough so that the input port 94 is disposed in a relatively wide portion of the vasculature, such as the celiac artery 90A (i.e., before the left gastric artery 90B branches off from the splenic and common hepatic arteries, both illustrated schematically as 90C), or even the aorta (not shown). This arrangement will make it even easier for the blood to flow into the input port 94, so that the blood flow can direct the particles to their desired destination.

Figure 9B:
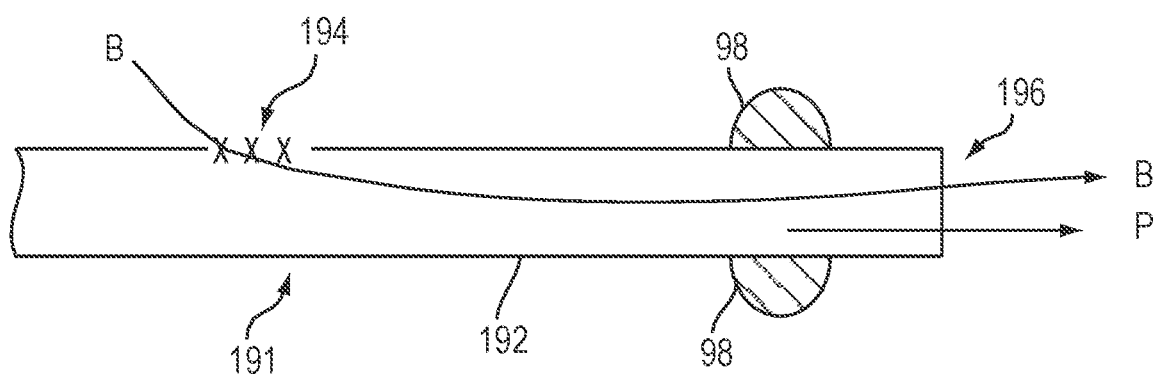
FIG. 9B depicts the distal end of another embodiment of an improved catheter that is designed to prevent reflux.

FIG. 9B depicts the distal end of an alternative novel catheter that is designed to maintain sufficient blood flow to carry the particles to their desired destination, while preventing reflux of the particles. In this embodiment, the wall 192 of the catheter 191 defines an internal lumen, and the particles are delivered through that internal lumen, as indicated by the arrow labeled P. The internal lumen provides a path for particles to flow between the proximal end of the catheter and the distal end of the catheter. The outer diameter of the catheter 191 is preferably between 0.026 and 0.052 inches, and is more preferably about 0.04 inches. The diameter of the internal lumen is preferably between 0.012 and 0.020 inches, and is more preferably about 0.016 inches. The internal lumen is preferably tracked over a guidewire (not shown) to facilitate safe positioning of the catheter 191 to the desired location. Optionally, longitudinally embedded core-wire (not shown) may be used as described above in connection with the FIG. 9A embodiment.

A balloon 98 that is similar to the balloon 98 of the FIG. 9A embodiment is also used in this FIG. 9B embodiment. When the balloon 98 is inflated, the natural flow of blood through the left gastric artery is blocked, which would ordinarily not be desirable because the blood flow help carry the particles along to their destination. To remedy this issue, an opening 194 into the first lumen is provided in the sidewall 192 of the catheter 191. This opening provides a path for blood to flow from the artery directly into the internal lumen of the catheter 191. The opening 194 is proximal to balloon 98, and the opening 194 permits blood to enter the internal lumen 191. The opening is disposed at a position such that when the distal end of the catheter is positioned in the target artery, blood from an artery in the patient's body can flow into the opening, through the internal lumen, and into the left gastric artery. Once inside the internal lumen 191, the blood will flow forward and will exit the internal lumen through output port 196, as indicated by the arrow labeled B-B. A strainer is disposed at the opening, and the strainer is configured to prevent the particles from exiting the first lumen via the opening. One preferred way to implement this strainer is to cover the opening 194 with a mesh similar to the mesh describe above in connection with FIG. 9A. Due to the mesh-covered opening 194, blood can flow forward through the artery even when the balloon 98 is inflated. This flow of blood will be sufficient to carry the particles along to their destination in the distal portion of the left gastric artery. In some preferred embodiments, the opening 194 is disposed far back enough along the catheter so that it will be disposed in a relatively wide portion of the vasculature, such as the celiac artery or even the aorta (not shown). This arrangement will make it even easier for the blood to flow into the opening 194 so that the blood flow can carry the particles to their desired destination in the left gastric artery. Note that any of the alternative strainers described above in connection with the FIG. 9A embodiment may also be used in this FIG. 9B embodiment.

Note that while the embodiments described above are described in the context of the left gastric artery, similar techniques may be used in other arteries to embolize different portions of a patient's anatomy. The artery into which the embolization material is delivered is referred to herein as the target artery.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

We claim:

1. A catheter for delivering embolization particles to a target artery of a patient, the catheter having a distal end and a proximal end, the catheter comprising:
    a first lumen that provides a fluid-tight path for particles to flow between the proximal end of the catheter and the distal end of the catheter;
    a balloon located near the distal end of the catheter, wherein the balloon is configured so that when the balloon is inflated, the balloon prevents blood from flowing through the target artery;
    an inflation lumen that is used to inflate the balloon, the inflation lumen having a distal end that is in fluid communication with an interior of the balloon;
    a second lumen that has an input port that is located within the artery proximal to the balloon and an output port that is located distal to the balloon, wherein the second lumen is configured to provide a fluid-tight path for blood to flow from the input port to the output port; and
    a strainer that prevents the particles from flowing through the second lumen, wherein the strainer is fine enough to prevent particles with sizes between 300 and 500 μm from passing, wherein the strainer is coarse enough to permit all types of blood components to pass, and wherein the strainer comprises a mesh having a mesh spacing between 150 and 250 microns,
    wherein the input port is disposed at a position such that when the distal end of the catheter is positioned in the target artery, blood from an artery in the patient's body can enter the second lumen via the input port, flow through the second lumen, exit the second lumen via the output port, and flow from the output port into the target artery.

2. A catheter for delivering embolization particles to a target artery of a patient, the catheter having a distal end and a proximal end, the catheter comprising:
    a first lumen that provides a fluid-tight path for particles to flow between the proximal end of the catheter and the distal end of the catheter;
    a balloon located near the distal end of the catheter, wherein the balloon is configured so that when the balloon is inflated, the balloon prevents blood from flowing through the target artery;
    an inflation lumen that is used to inflate the balloon, the inflation lumen having a distal end that is in fluid communication with an interior of the balloon;
    a second lumen that has an input port that is located within the artery proximal to the balloon and an output port that is located distal to the balloon, wherein the second lumen is configured to provide a fluid-tight path for blood to flow from the input port to the output port; and
    a strainer that prevents the particles from flowing through the second lumen, wherein the strainer is fine enough to prevent particles with sizes between 300 and 500 μm from passing, wherein the strainer is coarse enough to permit all types of blood components to pass, and wherein the strainer comprises a mesh having a mesh spacing between 150 and 250 microns, wherein the input port is disposed at a position such that when the distal end of the catheter is positioned in the target artery, blood from an artery in the patient's body can enter the second lumen via the input port, flow through the second lumen, exit the second lumen via the output port, and flow from the output port into the target artery, wherein the strainer is disposed at the input port of the second lumen.

3. The catheter of claim 1, wherein the strainer is disposed at the output port of the second lumen.

4. The catheter of claim 1, wherein the target artery is a left gastric artery, and wherein the distal end of the catheter and the balloon are configured for insertion into the left gastric artery.

\* \* \* \* \*